US006103503A

United States Patent [19]

[11] Patent Number: 6,103,503

[45] Date of Patent: Aug. 15, 2000

Kluttz et al.

[54] METHOD AND APPARATUS FOR CARRYING OUT NUCLEIC ACID AMPLIFICATION REACTIONS WITHIN A POROUS ABSORBENT MATERIAL

[75] Inventors: Bryan W. Kluttz, Norwell; Arthur L. Garland, Carver; Geoff A. McKinley; Luigi Catanzariti, both of Duxbury, all of Mass.

[73] Assignee: bio Mérieux, Inc., Hazelwood, Mo.

[21] Appl. No.: 09/107,352

[22] Filed: Jun. 30, 1998

Related U.S. Application Data

[63] Continuation of application No. 08/771,940, Dec. 23, 1996, abandoned.

[51] Int. Cl.[7] .......... C12P 19/34

[52] U.S. Cl. .......... 435/91.2; 435/287.7; 422/68.1; 422/102; 422/104

[58] Field of Search .......... 435/91.2, 287.7; 422/68.1, 102, 104

[56] References Cited

U.S. PATENT DOCUMENTS

| | | | |
|---|---|---|---|
| 3,951,748 | 4/1976 | Devlin | 195/103.5 R |
| 4,909,992 | 3/1990 | Bjorkman | 422/100 |
| 5,352,410 | 10/1994 | Hansen et al. | 422/58 |
| 5,604,101 | 2/1997 | Hanley et al. | 435/6 |
| 5,616,478 | 4/1997 | Chetverin et al. | 435/91.2 |
| 6,007,990 | 12/1999 | Levine et al | 435/6 |

FOREIGN PATENT DOCUMENTS

| | | |
|---|---|---|
| 0459093 | 12/1991 | European Pat. Off. . |
| 0724909 | 8/1996 | European Pat. Off. . |
| 0734767 | 10/1996 | European Pat. Off. . |
| 0738733 | 10/1996 | European Pat. Off. . |
| 0295069 | 12/1998 | European Pat. Off. . |
| 4410633 | 7/1995 | Germany . |

OTHER PUBLICATIONS

Database WPI Derwent Publications AN 96–285502, 1996 "Chetverina et al. Multiplication of Nucleic Acids—with Immobilization of the Medium . . . " XP002062012.

Database WPI Derwent Publications AN 91–113287, 1991 Fuso Yakuhin Kogyo "Nucleic Acid Amplification, Detection and Kit—by adsorbing on adsorbing agent, treating RNA sample on agent with reverse transcriptase, treating by enzyme amplification, and detecting . . . " XP002062013.

Publishec PCT document WO 96 28715 A, Sep., 1996.

Parik et al., "A Manifold Support for Molecular Genetic Reactions", Analytical Biochemistry, vol. 211, No. 1, May 15, 1993, pp. 144–150.

Published PCT document WO 95 17965 A, Jul. 6, 1995.

International Search Report for PCT patent application PCT/US 97/21850, dated Apr. 24, 1998.

*Primary Examiner*—Kenneth R. Horlick
*Attorney, Agent, or Firm*—McDonnell Boehnen Hulbert & Berghoff

[57] ABSTRACT

A testing apparatus is described that contains a test sample and one or more reagents, or reaction solutions associated with chemical reactions and a resilient, compressible, porous material, and which is amenable to subsequent process or reaction steps or liquid transfer steps. A piece of sponge or foam rubber, which is compatible with the amplification reactions and amplification products, is introduced into the reaction vessel and absorbs the test sample and reagents, or reaction solutions associated with an amplification process, or amplification products thus, reducing their loss through aerosolation.

14 Claims, 3 Drawing Sheets

| CHL TMA/HPA CONTROL (+) RLU'S | CHL TMA/HPA CONTROL (-) RLU'S | CHL TMA/HPA FOAM (+) RLU'S | CHL TMA/HPA FOAM (-) RLU'S |
|---|---|---|---|
| 2686876 | 13873 | 2119129 | 2818 |
| 2235645 | 2977 | 2514412 | 6551 |
| 2898143 | 9542 | 2648751 | 9873 |
| 2578210 | 10128 | 2245833 | 2463 |
| 2054346 | 3549 | 2715463 | 6548 |
| 2984322 | 5713 | 2375857 | 3243 |
| 2673255 | 6453 | 2086993 | 10233 |
| 2036465 | 8694 | 2568729 | 4681 |
| 2105468 | 2641 | 2348962 | 5642 |
| 2568433 | 3568 | 2482354 | 9785 |

| VOLUME PLACED IN TUBE (μL) | APPROXIMATE VOLUME LEFT IN TUBE AFTER INVERSION (μL) (NO FOAM) | APPROXIMATE VOLUME LEFT IN TUBE AFTER INVERSION (μL) (WITH FOAM) |
|---|---|---|
| 200 | 4 | 200 |
| 200 | 3 | 200 |
| 200 | 5 | 199 |
| 200 | 6 | 200 |
| 200 | 4 | 200 |
| 200 | 2 | 199 |
| 200 | 8 | 200 |
| 200 | 4 | 198 |
| 200 | 3 | 200 |
| 200 | 6 | 200 |
| 200 | 5 | 200 |

METHOD AND APPARATUS FOR CARRYING OUT NUCLEIC ACID AMPLIFICATION REACTIONS WITHIN A POROUS ABSORBENT MATERIAL

This is a continuation of application Ser. No. 08/771,940 filed Dec. 23, 1996, abandoned.

BACKGROUND OF THE INVENTION

A. Field of the Invention

This invention relates generally to an air matrix material for use in chemical reactions to compartmentalize reagents and/or reaction products of such chemical reactions which are amenable to subsequent process or reaction steps or transfer steps. Specifically, this invention relates to the method of synthesizing multiple copies of a target nucleic acid sequence within an air matrix material in order to reduce the loss of reagents or reaction solutions associated with these amplification reactions and more particularly to reduce from the test container the aerosolation of amplification products produced from these reactions.

B. Technical Disclosure

When an abundant supply of starting materials is available, nucleic acid target sequences are readily detectable by common hybridization techniques following extraction. Several sensitive amplification techniques have been developed to allow detection of target sequences from very small amounts of starting material. The most notable of these methods include Polymerase Chain Reaction (PCR), Transcription Mediated Amplification (TMA), and Nucleic Acid Sequence Based Amplification (NASBA). These techniques produce either a logarithmic or exponential increase in the number of target sequences or amplicons. Out of all of these methods, the most widely used method is PCR, which uses primer-dependent synthesis of complementary nucleic acids by thermally stable DNA polymerase to produce copies of the target sequence. Repeated cycling between the optimal temperatures for annealing of the primers, extension by the polymerase and denaturation of the duplex nucleic acids produces an exponential accumulation of copies of the original target sequence. Usually this repeated cycling is carried out in stoppered plastic tubes, such as Eppendorf® tubes or other appropriate containers. Once the desired number of amplicons have been produced during cycling, these stoppered tubes are reopened for fluid transfer. It is during this act of unstoppering the reaction tubes and transferring of reaction fluids or products that aerosols may be created and released. These aerosols which are then dispersed into the environment can contain amplicons such as DNA which can easily contaminate other reactions.

Another problem presented in these and other reactions is retaining reagents, reaction solutions, and reaction products in a definable space for chemical reactions in general, particularly where there is some risk of contamination from dispersal of such products.

More recently, TMA and NASBA were developed that make possible the exponential amplification of single stranded nucleic acid targets at a single temperature. Both techniques involve the incorporation of an RNA polymerase promoter sequence into the target nucleic acid sequence. This promoter subsequently directs transcription by an RNA polymerase to make multiple RNA copies of the original target sequence. Using reverse transcriptase and RNase H activities, each amplicon can serve as a target molecule for subsequent amplification, allowing the reaction to cycle at a constant temperature.

In theory, the use of amplification techniques allows for the detection of a single target molecule, although more practical estimates suggest that ten to one or several hundred molecules are routinely necessary in a test sample. While it is the intent of each of the above techniques to increase the amount of the target sequence or amplicon by many orders of magnitude, the abundance of such reaction products can be problematic if they are not retained in definable space.

Equally important in performing these types of reactions is maintaining the proper activity and volume requirements for subsequent identification and detection procedures; since amplicons, reagents, and reaction solutions can be easily lost or aerosolized, by transfer steps. The loss of aerosols from the reaction solution can easily contain up to one million copies of molecules, each of which can act as a target molecule for an unintentional amplification and the loss of volume of reagents and reaction solutions may negatively affect the test process.

To deal with this contamination problem, laboratories have tried a variety of measures. These measures include stringent cleaning with caustic reagents such as sodium hypochlorite in between each run of an amplification reaction or of maintaining separate work sites for setting up and for running the reactions.

The present invention addresses the problem(s) by demonstrating that nucleic acid amplification can occur within the matrix of a porous, absorbent material, such as foam rubber or a sponge, which can reduce the spread of amplification products and the loss of reagents and reaction solutions outside the test vessel. This invention advantageously controls the unwanted loss of reagents and reaction solutions, as well as, the distribution of contaminating molecules. This invention also demonstrates that the use of an air matrix is compatible with amplification reactions.

SUMMARY OF THE INVENTION

The exponential amplification of nucleic acids produces a large number of amplification products which present a problem if they inadvertently contaminate surrounding surfaces and, possibly thereafter, subsequent assays. Thus, there is a need for a product and/or technique for containing the amplification products of these enzymatic or autocatalytic techniques without interfering with the efficiency or specificity of said techniques. In addition, there is also a general need for a product and/or technique for containing the amplification reagents or reaction solutions within the reaction vessel.

Accordingly, it is a primary object of the present invention to provide a product and/or method of absorbing the test sample and one or more reagents, or the reaction solutions, and amplification products within an air matrix material like a sponge or foam rubber or similar porous material which is resilient and compressible from which the amplification products can be later withdrawn using a pipetor or similar instrument. The sponge or foam rubber retains the amplification products within an air matrix inside the sponge or foam rubber and reduces unwanted aerosolation and contamination of the amplification products and loss of volume during the transfer of the various solutions involved in the chemical reactions.

It is a further object of the present invention to trap or absorb the test sample and one or more reagents, or reaction solutions, and generated reaction products within the sponge or foam rubber thereby allowing further reactions to occur while simultaneously reducing the spread of reagents, reaction solutions, and reaction products outside of the reaction container and otherwise controlling the unwanted distribution of such elements.

The present invention includes a material for containing accumulated amplification products within a defined space.

A liquid phase reaction medium is absorbed by the material of the present invention, when placed in a reaction vessel.

Another characterization of the invention provides an air matrix material like sponge or foam rubber or a similar porous material which is resilient and compressible for use in performing amplification reactions. This air matrix material absorbs the test sample and one or more reagents, or the reaction solutions, and the accumulated generated amplification products within the air matrices of the material. While containing the amplification products, reagents, or reaction solutions within the air matrices, the material reduces aerosolation and thus contamination of amplification products and the loss of volume.

Another characterization of the invention includes a testing array for containing a test sample and one or more reagents, or reaction solutions associated with an amplification process, and accumulated amplification products. This testing array comprises a device with at least an area which contains a liquid phase reaction medium of a test sample and one or more reagents, or reaction solutions associated with the amplification process and a porous resilient absorbent material placed within the reaction area in contact with the liquid phase reaction medium. The porous resilient absorbent material absorbs and retains the liquid phase reaction medium wherein a reaction, i.e., amplification, process occurs and also reduces the release of the products from the reaction area.

Another characterization of the invention includes a method of reducing contamination of the reaction products, reagents, or reaction solutions in a test reaction. This method comprises the steps of inserting a porous material which is resilient and compressible into a sample container in contact with the liquid test sample and one or more reagents, or reaction solutions; in order to absorb the reaction products within the porous material; and subsequently withdrawing the reaction products from the porous material with an implement contacting the porous material. The porous material contains the accumulated reaction products and reduces their release from the test sample container.

These and other objects in view, as will be apparent to those skilled in the art, the invention resides in the combination of elements set forth in the specification and covered by the claims appended hereto.

BRIEF DESCRIPTION OF THE DRAWINGS

The foregoing and other objects and advantages of the invention is illustrated in the drawings, wherein like reference numerals refer to like statements in the various views, and wherein.

DETAILED DESCRIPTION

Figure 1:
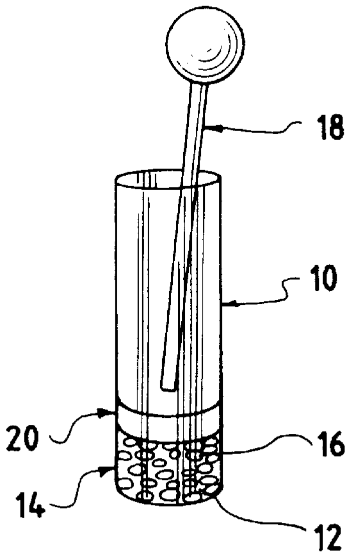
FIG. 1 is an elevation view of a reaction vessel illustrating a porous material placed within a test tube containing a liquid phase reaction medium and further illustrating an optional oil phase layer and the insertion of a pipette into the test tube to remove reaction products from the porous material.

An embodiment of the testing apparatus for containing accumulated reaction products, or reagents, or reaction solutions within a defined space is illustrated in FIG. 1. A reaction vessel 10, which may consist of a test tube, microtiter plate, petri dish or other suitable reaction area is provided with a liquid phase reaction medium 12 and an air matrix material 14 and an optional oil phase layer 20. The volume of liquid phase added must be of a volume that can be fully absorbed by the air matrix material. It is preferred that the air matrix material be sized to fully absorb the liquid phase but not so saturated that fluid can be extracted from the air matrix material without contact by a pipette or other suitable fluid transfer device or mechanism, i.e., by simple compression of the air matrix material or that the further addition of another liquid of a small volume could not also be absorbed. This liquid phase reaction medium in a preferred chemical reaction contains a test sample and one or more reagents or reaction solutions associated with an amplification process. The amplification product may be amplicons or any amplified other target molecule. The methods of producing amplification products may include the Polymerase Chain Reaction (PCR), Transcription Mediated Amplification (TMA), and Nucleic Acid Sequence Based Amplification (NASBA™), or other similar reactions.

The porous material 14 is preferably resilient, compressible and absorbent and may comprise a piece of sponge or foam rubber or any other suitable porous material. A sized piece of sponge 14 may be made from either natural or synthetic materials. The porous material should have surface characteristics including, for example, a plurality of apertures 16 on its surface and/or open cavities within or on the body of the sponge 14. The cavities define the confines into which the liquid phase is absorbed and the chemical reactions occur.

Figure 3:
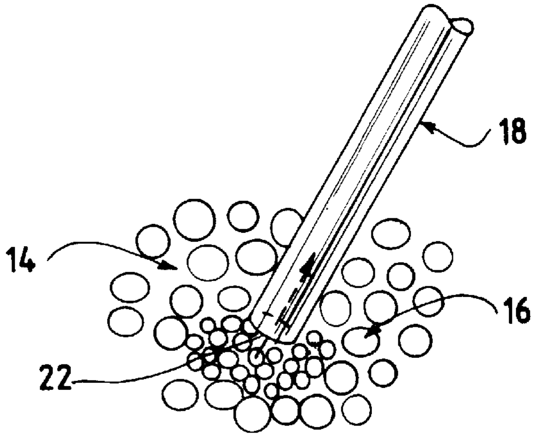
FIG. 3 is an enlarged view of a representative porous material illustrating that the reaction products are extracted from the air matrix of the porous material by a pipette by compressing the material.

Once the porous material comes in contact with a liquid phase reaction medium, including, for example, a test sample, enzymes, or other reagents, the liquid medium is absorbed by the porous material through the apertures or cavities on the surface of the porous material and into the air matrix. It is preferred that the liquid phase is fully absorbed but does not saturate the porous material. The liquid phase reaction medium containing such reagents, or reaction solutions is now absorbed or contained within the matrix of the material, thereby advantageously reducing the possible loss of test sample, reagents, or reaction solutions and subsequent reaction products, i.e., amplicons from the porous material during the reaction process and procedure steps. The forces acting to resist the movement of the liquid from the matrix of the porous material are the result of the decreased force of the weight of the volume of liquid. That is, by decompartmentalizing the liquid, the porous material decreases the force the liquid's surface tension must overcome in order to remain absorbed. Thus, with the force of the weight of the liquid decreased, the liquid remains more easily within the material disposed in the container or reaction area. The contained reaction products can later be withdrawn by a pipette 18 or other suitable implement, as depicted with the direction arrows 22 (FIG. 3). In another embodiment of the present invention where the reaction solution is heated, oil 20 is overlaid the porous material which helps reduce loss of volume of the liquid phase due to evaporation.

Figure 2:
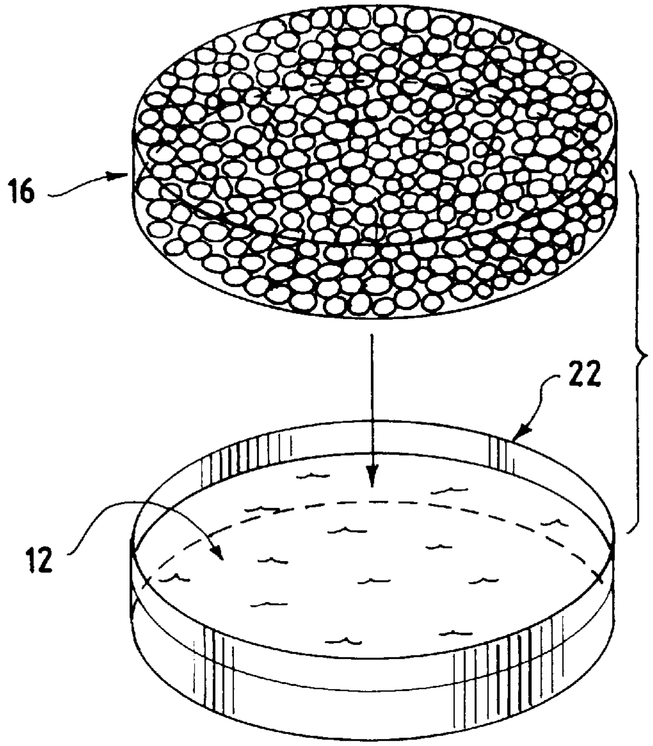
FIG. 2 is an elevation view of a petri dish illustrating a porous material in contact with a liquid reaction medium.

Referring to FIG. 2, the use of a petri dish 22 as the reaction area with the present invention is illustrated. Again, a liquid phase reaction medium 12 producing reaction products other than amplification products is placed within the petri dish 22. The flexible porous material 16 is then placed into the petri dish 22 in contact with the reaction medium 12. The porous material can of course be placed into the petri dish before addition of a test sample and the porous material may be previously contacted with reagents before the introduction of the test sample. Absorption of the test sample, reagents, or reaction solutions from the liquid phase reaction medium 12 within the porous material 16 occurs, thereby reducing the potential loss of volume and resulting contamination of the testing zone. The contamination may be particularly problematic for maintaining a clean work site and could adversely effect subsequent or other ongoing chemical reactions. The testing zone can be broadly defined as being outside of the reaction area or container. The reaction product may be extracted and further steps or reactions can then be performed, i.e., detection, identification, amplification, etc.

Referring now to FIG. 3, an enlarged view of the withdrawal of reaction products, i.e., amplicons, is illustrated. With this figure, it can be appreciated that the cavities of the porous material 14 stores the amplification or reaction products and that they must be withdrawn or compressed from the porous material by the use of a pipette 18 or other physical means. By compressing the porous material 14 with the pipette 18, the reaction products can be extracted out of the area 16 into the pipette, in the direction 22 illustrated by the arrows. The extracted reaction or amplification products can now be transferred to another reaction tube or to other apparatus.

Another embodiment of the present invention uses a microtiter plate (not shown) or another device containing greater than one test reaction well, as the reaction area 10. The microtiter plate comprises a plurality of reaction wells. A liquid phase reaction medium 12 containing a test sample and one or more reagents is placed within the wells of the microtiter plate. The absorbent material 14 is then placed within each of the reaction wells in contact with the liquid phase reaction medium 12. Absorption of the test sample and one or more reagents, or reaction solutions from the liquid phase reaction medium 12 within the porous material 14 occurs, thereby minimizing loss of test sample, reagents, or reaction solutions.

In another embodiment the reaction well may consist of a plastic pouch (not shown) with one or more openings that incorporates the air matrix material to concentrate the reaction solutions during the reaction and wherein the pouch may be compressed to remove the various reaction products or to facilitate mixing of the reaction solutions by compressing the material.

In another embodiment the air matrix material may have absorbed or covalently attached reagents necessary for performing a desired reaction or for retaining biological materials not desired to be removed from the air matrix material after completion of the desired reaction.

EXAMPLE 1

In this example, one milliliter of water is placed in a test tube one centimeter in diameter. The force exerted by the surface tension and the weight of the water was calculated both with and without the presence of the air matrix material in the test tube. The force due to the surface tension of the liquid is a product of the surface tension (γ) and the physical dimension of the length (L) of the contact between the interface of the fluid and the vessel containing the fluid and is represented as follows: $F=\gamma L$ (Equation 1). Since the length of the physical contact (L) in this example is equivalent to the circumference of the tube, the force due to the surface tension is represented by Equation 1 as follows: $F=\gamma\pi d$ (Equation 2). Applying Equation 2 and using the value of the surface tension between water and air at 20° C. at one atmosphere of pressure to be $7.28\times10^{-2}$ N/m and π to be 3.14159 we find that F=0.0091 Newtons (N).

The force acting to move the liquid from the vessel, i.e., the weight (W) of the water, is the product of the density (ρ) of water, the attraction of gravity (g), and the volume (V). At 20° C. and at sea level (one atmosphere of pressure), this force can be represented as follows: $W=\rho g V$ (Equation 3). Applying Equation 3, we find $W=(10^3 \text{ kg/m}^3)(9.8 \text{ m/s}^2)(1\times10^{-6}\text{m}^3)=0.0098$ N. Therefore, because the force of the water is greater than the force of the surface tension the water falls out of the container, when the container is inverted.

The introduction of an air matrix material obtained from any available source into the same container including the milliliter of water produces a different result. The addition of the material which fully absorbs the water reduces the volume of the one milliliter of water to a volume defined by the average pore size of the material. The air matrix material added in this example possessed a measured pore diameter equal to 1 millimeter or $1\times10^{-3}$. This is quantified by using the equation for the volume of a sphere which is equal to $4/3(\pi r^3)$ or $5.2\times10_{-10}\text{m}^3$ for this example. By substituting this volume into the Equation 3 for calculating the force exerted by the weight of the liquid, this force now equals 0.000051 N. Thus, the force acting to move the water out of the container is reduced approximately 200-fold. Similarly, the force due to the surface tension is reduced, but only by a factor of ten which is calculated by substituting the average pore diameter into Equation 1. Since the force due to surface tension is now greater with the addition of the air matrix material than the force exerted by the weight of the water, the water remains inside the container, when inverted.

In summary, inserting an air matrix material of foam rubber or other absorbent material into a given volume of liquid reduces the effective weight of the liquid significantly. This reduction in liquid weight acts to lower the force which the surface tension must overcome in order to retain the given fluid inside the container. Therefore, the porous material acts as a barrier against undesirable dispersion of fluids, as would occur for example during process or reaction steps of a liquid phase reaction medium.

EXAMPLE 2

By way of example, the air matrix material of the present invention was utilized to perform the Chlamydia TMA assay according to instructions provided by the manufacturer. The assay is commercially available from Gen-Probe®, San Diego, Calif. Foam rubbers of varying pore size were used in this example and demonstrated that the neither density nor pore size of the foam appears to influence the amplification efficiency of the TMA reaction. However, the foam rubber was found to influence the retention of the liquid within the reaction vessel. This retention benefit was further apparent with the use of colored solutions in the amplification reactions. With the use of foam rubber within the colored reactions, no leakage or spillage was detected even with the inversion of the uncovered tubes or containers.

Briefly, the reaction was assembled by combining 100 μL of positive Chlamydia control or 100 μL negative control with 50 μL of Gen-Probe amplification buffer in test tubes (n=12) containing varying appropriate mass or volume of air matrix material 14. In this specific experiment either a tube with an amount of foam rubber was utilized sufficient to tightly fit within the tube and fully absorb the liquid (i.e., dimensions approximately equal to the 200 μL of total reaction volume) or a tube without any foam rubber. This mixture was heated to 95° C. for five minutes then cooled in a 42° C. waterbath for five minutes. 50 μL of enzyme solution was then added to each tube and the mixture was incubated at 42° C. for one hour. After one hour, 50 μL was removed from each sample and placed in a separate tube for analysis using Gen-Probe's commercially available Hybridization Protection Assay (HPA). To perform HPA on these samples, 50 μL of Gen-Probe acridium ester probe reagent was added to these tubes and incubated at 60° C. for 10 minutes. 150 μL of Gen-Probe Selection reagent was then added to each tube and the tubes were again incubated at 60° C. for 10 minutes. The reactions were then read on the Gen-Probe luminometer for two seconds.

Figures 4, 5:
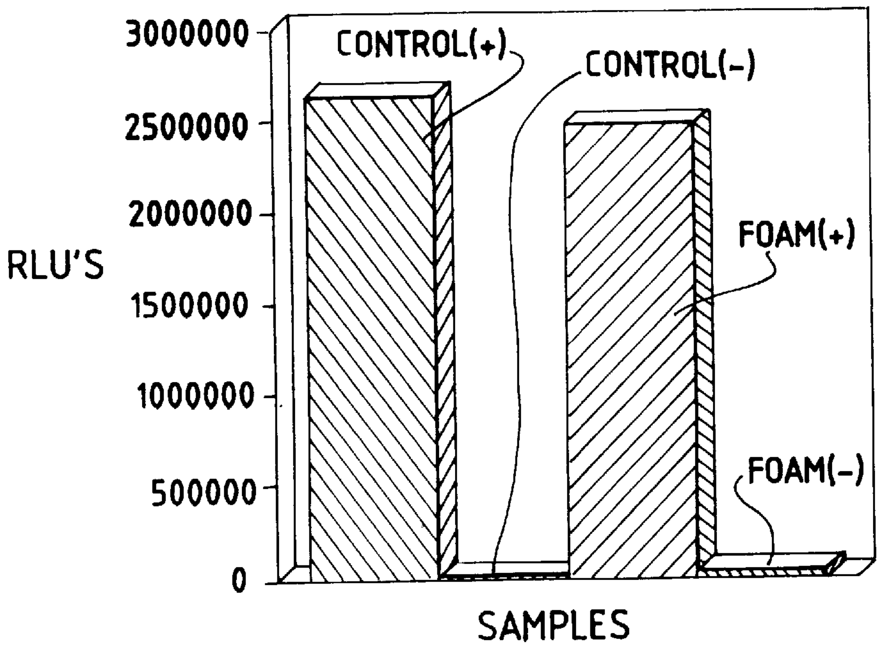
FIG. 4 is a table of the Relative Light Units (RLU) of the commercially available Gen-Probe Hybridization Protection Assay or HPA reactions of Chlamydia TMA read on the Gen-Probe Leader Luminometer with and without the presence of air matrix material.
FIG. 5 is a graph of the commercially available Gen-Probe Hybridization Protection Assay or HPA reactions of Chlamydia TMA read on the Gen-Probe Leader Luminometer with and without the presence of air matrix material.

The effect of an air matrix material on TMA amplifications are summarized in FIG. 4 which shows the HPA reaction results in relative light units (RLU) of the Chlamydia TMA reactions as read on the Gen-Probe Leader Luminometer. The Gen-Probe positive control, Control(+), (0.5 femtograms (fg) of Chlamydia trachomatis ribosomal RNA/TMA reaction) and the Gen-Probe negative control, Control (−), (0.5 fg of Mycobacterium tuberculosis) was run according to the standard Gen-Probe protocol, i.e., in a polypropylene reaction tube and overlaid with Gen-Probe's silicone oil. Similar reactions without an overlay of oil were set up for each of the Control(+) and Control(−) reactions with an appropriate size piece of foam rubber inserted into the tubes, i.e., a piece of foam having the dimensions to accommodate the 200 μL volume of the reaction and of such dimensions to fit tightly inside the tube. These parallel reactions are denoted Foam(+) and Foam(−) respectively. Eleven data points for all four reaction were recorded and represented by the average RLU reading.

FIG. 4 shows that the TMA amplification is not affected by the presence of the foam rubber. The foam neither inhibited the reaction, i.e., comparable results in positive reactions, Foam (+) and Control (+), nor contributed to contamination resulting in cross-reacting, nonspecific amplification products as would had been indicated by high values in the negative reactions (Foam (−)). Subsequently, all the replicates (n=11) were pooled and the standard error calculated and graphed (see FIG. 5).

Figures 6, 7:
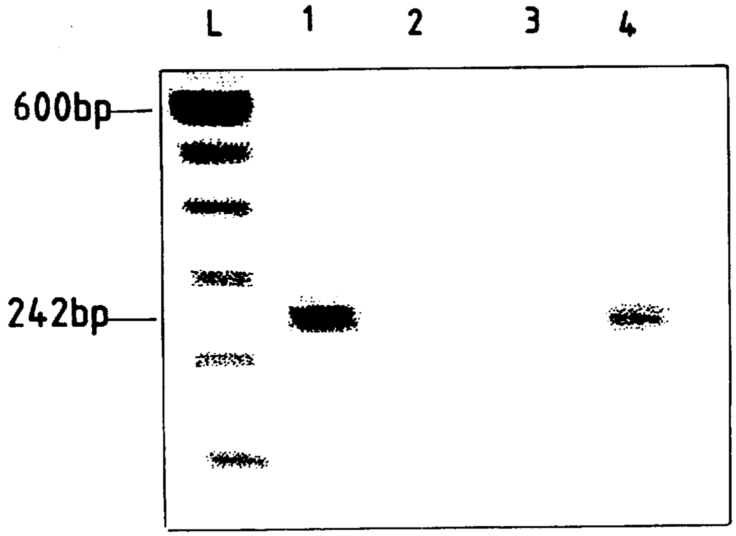
FIG. 6 is a table of the amount of liquid retained in the inverted reaction tubes both with and without foam rubber.
FIG. 7 is the digitally inverted image of an ethidium bromide-stained agarose gel of the PCR amplification of Chlamydia trachomatis cryptic plasmid.

At the end of the experiment, all tubes were inverted and the volume of aqueous fluid retained in the tube was measured. FIG. 6 shows that nearly all the fluid was retained in those tubes containing the foam rubber while nearly all volume was lost in the tubes without foam rubber.

EXAMPLE 3

Following the steps as set forth in Mahony et al. (1990), Chlamydia PCR reactions were set up in parallel to allow the amplification of the cryptic plasmid of Chlamydia trachomatis. Briefly, the "KL1" and "KL2" primers were used to amplify a 242 base pair (bp) portion of the cloned cryptic plasmid using 1.5 mM $MgCl$, 0.2 mM of each deoxynucleosidetriphosphate (dNTP), 10 mM Tris-HCI buffer (pH=8.3), 40 mM KCl, and 1 μL. Reactions were run with and without 10 picograms (pg) of cryptic plasmid DNA in either the presence and absence of the same foam rubber 14 used in the previous example. In positive reactions containing the foam rubber 14, one tube was overlaid with 100 μL of mineral oil 20 to reduce loss of volume due to evaporation, and one tube was not. After a 5 minutes "hot start" (94° C.), 1.5 units of Taq thermostable DNA polymerase (Perkin Elmer,) were added to each reaction. Amplification was conducted in a Perkin-Elmer thermocycler for 34 cycles under the following cycle conditions: 1.0 minute at 94° C. for denaturation, 1.0 minute at 55° for primer annealing and 1.0 minute at 72° C. for polymerase extension. Following amplification, 10 μL of each sample were electrophoresed through a 1.0% agarose gel in the presence of ethidium bromide. The methodologies utilized in this example were those as recommended by Perkin Elmer.

To evaluate the effect that the air matrix material would have on a PCR amplification, an experiment was set up using a known target sequence and the appropriate primers. FIG. 5 provides an image of the ethidium bromide-stained agarose gel of the PCR reaction products that was captured digitally and with a CCD camera (Connectix Corp., 2655 Campus Drive, San Mateo, Calif. 94403) and inverted with NIH Image software (NIH Image Version 1.58b33, freeware downloaded from http://rsb.info.nih.gov/nih-image/download.html). The positive control reaction consisted of a standard PCR amplification overlaid with mineral oil and run without the addition of air matrix material. This positive control reaction was loaded into Lane 1 of the agarose gel for analysis. The 242 bp band is the expected product of the positive control reaction and is determined by comparison with the 100 bp molecular weight marker (Gibco Biological Research Laboratories, Gaithersburg, Md., USA) run in the lane marked "L". The negative control reaction consisted of a standard PCR amplification without the addition of the cryptic plasmid and with the addition of a sufficient amount of foam rubber to absorb the reaction solution. The negative control reaction was loaded into Lane 2 of the agarose gel for analysis. The reaction solutions loaded into Lane 3 and Lane 4 consisted of standard PCR amplifications which included the addition of air matrix material. Also, the reaction solution loaded into Lane 3 did not include an overlay of mineral oil during amplification while the reaction solution loaded into Lane 4 did include a layer of mineral oil. The results visualized in the ethidium stained agarose gel suggest that it is possible to perform the PCR reaction in the presence of the air matrix material, if the evaporation of the reaction solution is controlled by using mineral oil to overlay the reaction. Although the band observed in the reaction that included both the foam rubber and the mineral oil is fainter than the one in the positive control reaction, any difference in reaction efficiency was likely exaggerated due to uneven manual loading of the reaction samples onto the agarose gel.

It is to be understood that various other modifications will be apparent to and can readily be made by those skilled in the art, given the disclosure herein, without departing from the scope and materials of this invention. It is not, however, intended that the scope of the claims appended hereto be limited to the description as set forth herein, but rather the claims be construed as encompassing all features of patentable novelty which resides in the present invention, including all features which would be treated as equivalents thereof to those skilled in the art to which the invention pertains. It is also noted that the examples are intended to illustrate, and not to limit the invention.

We claim:

1. A testing apparatus for containing or absorbing a test sample and one or more reagents, or reaction solutions associated with a chemical reaction, the apparatus comprising:

a liquid phase reaction medium including a test sample and one or more reagents, or reaction solutions associated with a chemical reaction;

a reaction vessel for containing said liquid phase reaction medium; and a porous material, said porous material placed within said reaction vessel in contact with said liquid phase reaction medium in order to contain and substantially fully absorb said liquid phase reaction medium, wherein said chemical reaction occurs within said porous material and said liquid phase reaction medium; and wherein said chemical reaction comprises an amplification process or reaction which generates amplification products; and wherein said liquid phase reaction medium, when substantially fully absorbed in said porous material, remains unbound to said porous material and in a free liquid state such that said amplification products may be readily extracted from said porous material in a liquid phase by compression of said porous material and suction of said amplification products in said liquid phase into a suitable implement, whereby the performance and containment of said amplification reaction within said porous material substantially prevents escape of said amplification products from said reaction vessel and minimizes contamination of surfaces external from said reaction vessel.

2. The testing apparatus as recited in claim 1, wherein said porous material includes apertures and internal cavities, whereby said apertures allow said test sample and reagents, or said reaction solutions, to enter said apertures and internal cavities, and said apertures and internal cavities also allow said test sample and reagents, or reaction solutions, to be removed from said porous material.

3. The testing apparatus as recited in claim 1, wherein said amplification product comprises an amplicon.

4. The testing apparatus as recited in claim 1, wherein said porous material comprises a resilient or compressible material selected from the group of materials consisting of sponge, foam rubber, and plastic.

5. The testing apparatus as recited in claim 1, wherein said porous material is selected from the group of materials consiting of synthetic and natural materials.

6. The testing apparatus as recited in claim 1, wherein said reaction vessel comprises a vessel selected from the group of vessels consisting of a test tube, a microtiter plate, a pouch, and a petri dish.

7. A testing apparatus for containing or absorbing a test sample and one or more reagents, or reaction solutions associated with a chemical reaction, the apparatus comprising;

a liquid phase reaction medium including a test sample and one or more reagents; or reaction solutions associated with a chemical reaction, said chemical reaction producing reaction products;

a reaction vessel for containing said liquid phase reaction medium; and a porous material, said porous material placed within said reaction vessel in contact with said liquid phase reaction medium in order to contain and substantially fully absorb said liquid phase reaction medium, wherein said chemical reaction occurs within said porous material and liquid phase reaction medium, wherein said porous material is overlaid with mineral oil following absorption of said liquid phase reaction medium;

wherein said liquid phase reaction medium, when substantially fully absorbed in said porous material, remains unbound to said porous material and in a free liquid state such that said reaction products may be readily extracted from said porous material in a liquid phase by compression of said porous material and suction of said reaction products in said liquid phase into a suitable implement, whereby the performance and containment of said chemical reaction within said porous material substantially prevents escape of said reaction products from said reaction vessel and minimizes contamination of surfaces external from said reaction vessel.

8. The testing apparatus as recited in claim 1, wherein said porous absorbent material is resilient and has characteristics that allows said liquid phase reaction medium to enter and be absorbed by said porous absorbent material and to be removed from said porous absorbent material.

9. An amplification process testing array for containing a test sample and one or more reagents or reaction solutions associated with an amplification process, comprising:

a device comprising a plurality of reaction wells, each reaction well containing a liquid phase reaction medium including a test sample and one or more reagents, or reaction solutions associated with an amplification process; and a porous resilient absorbent material placed within at least two of said reaction wells in contact with said reaction medium, whereby said absorbent material fully absorbs said reaction medium and wherein said amplification process occurs in said liquid phase reaction medium to generate and accumulate amplification products such that said absorbent material reduces the release of said amplification products from said reaction well;

wherein said liquid phase reaction medium, when substantially fully absorbed in said porous material, remains unbound to said porous material and in a free liquid state such that said amplification products may be readily extracted from said porous material in a liquid phase by compression of said porous material and suction of said amplification products in said liquid phase into a suitable implement, whereby the performance and containment of said amplification reaction within said porous material substantially prevents escape of said amplification products from said reaction vessel and minimizes contamination of surfaces external from said reaction vessel.

10. A method of reducing the loss of amplification products, or contamination caused by amplification products following an amplification reaction, comprising said steps of:

a) introducing into a reaction vessel, reaction solutions associated with an amplification process wherein said reaction solutions define a reagent solution in a liquid phase reaction medium;

b) inserting a porous absorbent material into a reaction vessel to contact and absorb said reagent solution within said porous absorbent material; and c) performing said amplification process in said liquid phase reaction medium to generate amplification products, wherein said liquid phase reaction medium, when substantially fully absorbed in said porous absorbent material, remains unbound to said porous material and in a free liquid state such that said amplification products may be readily extracted from said porous absorbent material in a liquid phase by compression of said porous material and suction of said amplification products in said liquid phase into a suitable implement, whereby the performance and containment of said amplification reaction within said porous material substantially prevents escape of said amplification products from said reaction vessel and minimizes contamination of surfaces external from said reaction vessel.

11. The method as recited in claim 10, further comprising the step of withdrawing said amplification products from said porous absorbent material.

12. The method as recited in claim 11, further comprising the step of withdrawing said amplification products from said porous absorbent material with an implement inserted into said porous absorbent material.

13. The apparatus of claim 1, wherein said porous material is overlaid with mineral oil following absorption of said liquid phase reaction medium.

14. The method of claim 10, further comprising the step of overlaying said porous absorbent material with mineral oil after absorption of said reagent solution.

* * * * *